(12) United States Patent
Todor et al.

(10) Patent No.: US 9,381,003 B2
(45) Date of Patent: Jul. 5, 2016

(54) DIGITAL CONTROLLER FOR SURGICAL HANDPIECE

(71) Applicant: Integrated Medical Systems International, Inc., Birmingham, AL (US)

(72) Inventors: Marius Todor, Lake Worth, FL (US); Peter Pal Bodor, Pembroke Pines, FL (US); Shusheng Ye, Davie, FL (US)

(73) Assignee: Integrated Medical Systems International, Inc., Birmingham, AL (US)

( * ) Notice: Subject to any disclaimer, the term of this patent is extended or adjusted under 35 U.S.C. 154(b) by 525 days.

(21) Appl. No.: 13/849,291

(22) Filed: Mar. 22, 2013

(65) Prior Publication Data

US 2013/0297074 A1 Nov. 7, 2013

Related U.S. Application Data

(60) Provisional application No. 61/614,921, filed on Mar. 23, 2012.

(51) Int. Cl.
| | |
|---|---|
| G06F 19/00 | (2011.01) |
| A61B 17/00 | (2006.01) |
| G05B 19/04 | (2006.01) |
| A61B 17/32 | (2006.01) |
| A61B 17/16 | (2006.01) |
| A61B 19/00 | (2006.01) |

(52) U.S. Cl.
CPC ............. *A61B 17/00* (2013.01); *A61B 17/1626* (2013.01); *A61B 17/32002* (2013.01); *G05B 19/04* (2013.01); *A61B 2017/0046* (2013.01); *A61B 2017/00075* (2013.01); *A61B 2017/00084* (2013.01); *A61B 2017/00221* (2013.01); *A61B 2017/00398* (2013.01); *A61B 2019/467* (2013.01)

(58) Field of Classification Search
CPC ................. A61B 17/1626; A61B 2017/00017; A61B 17/00
USPC ......................................................... 700/275
See application file for complete search history.

(56) References Cited

U.S. PATENT DOCUMENTS

| | | | |
|---|---|---|---|
| 7,704,254 B2 * | 4/2010 | Walen ..................... | A61B 17/14 606/82 |
| 2002/0087179 A1 * | 7/2002 | Culp ................. | A61B 17/32002 606/167 |
| 2007/0085496 A1 * | 4/2007 | Philipp ................ | A61B 17/151 318/139 |

(Continued)

*Primary Examiner* — Michael D Masinick
(74) *Attorney, Agent, or Firm* — C. Brandon Browning; Maynard, Cooper & Gale, PC

(57) ABSTRACT

The present disclosure generally pertains to a digital controller for surgical handpieces. The controller is programmable and configurable by software which may be used with a variety of types of handpieces. The controller is equipped with environmental sensors that detect pressure, humidity and temperature, and operational sensors that detect the angle and placement of the rotor of a motor. These sensors provide data used for testing and evaluating the function of the handpiece. A filter program is provided which removes electronic noise from collected data. The controller includes an electronic memory writer and reader to download firmware, control parameters for handpiece operation and read logged data from sensors to determine motor function. The sensor includes a hermetic enclosure constructed from a heat conducting material and that is non-ferromagnetic to allow communication between the trigger and controller.

15 Claims, 16 Drawing Sheets

(56) References Cited

U.S. PATENT DOCUMENTS

| | | | |
|---|---|---|---|
| 2007/0250098 A1* | 10/2007 | Malackowski | A61B 17/1613 606/170 |
| 2009/0128330 A1* | 5/2009 | Monroe | A61B 19/026 340/568.1 |
| 2013/0245704 A1* | 9/2013 | Koltz | A61B 17/00 606/86 A |
| 2013/0297074 A1* | 11/2013 | Todor | A61B 17/00 700/275 |
| 2015/0201918 A1* | 7/2015 | Kumar | A61B 17/00 606/104 |

* cited by examiner

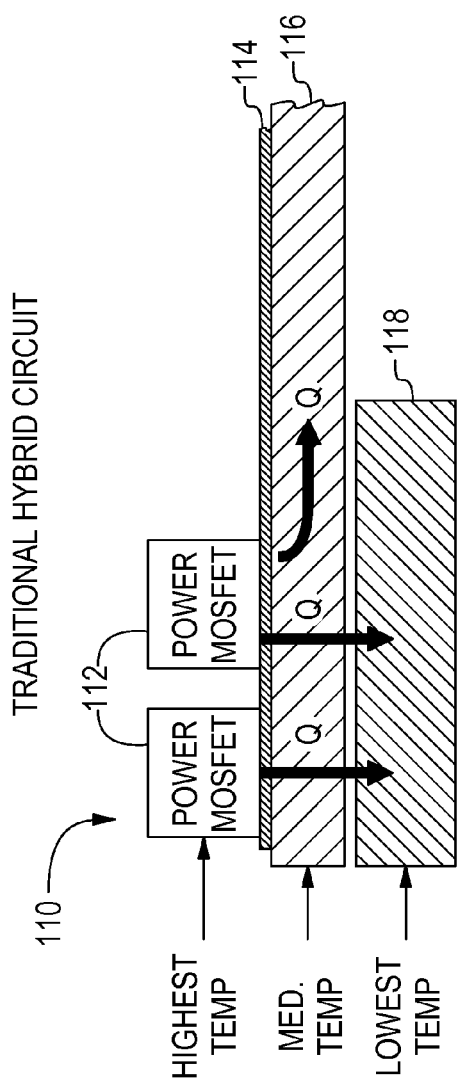
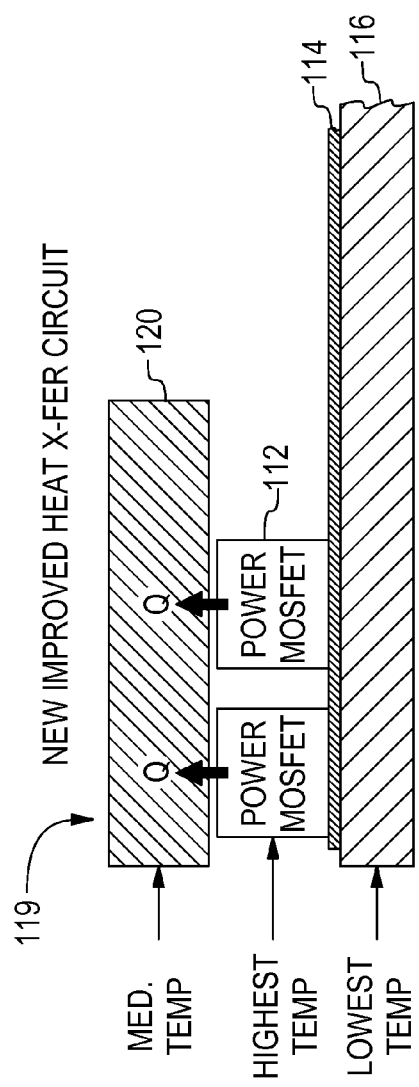

DIGITAL CONTROLLER FOR SURGICAL HANDPIECE

CROSS REFERENCE TO RELATED APPLICATION

This application claims priority to U.S. Provisional Patent Application No. 61/614,921, entitled "Digital Controller for Surgical Handpiece," filed on Mar. 23, 2012, which is incorporated herein by reference.

FIELD OF THE INVENTION

The present invention relates to a digital controller for surgical handpieces. Specifically, the invention provides for a dual processor digital controller that is software programmable and hardware configurable for use in the operation of various types of electric powered surgical handpieces.

BACKGROUND OF THE INVENTION

Surgical interventions often require specialized surgical instruments. These instruments must be durable, easy to clean and sterilize and compact in shape so as to not obstruct the view of the incision site. Many handpieces are powered to provide better cutting or drilling abilities. The handpiece may be AC-powered, water-powered, air-powered, or belt-driven, and may include a foot controller for regulation of speed and direction of rotation or a contra-angle attachment for difficult to reach areas.

Electric handpieces are increasing in popularity as they provide excellent power and torque over a wide range of speeds, allowing the operator to select the appropriate revolutions-per-minute (RPM) for the procedure at hand. By using attachments with different gear reduction ratios, one system can provide high-speed, slow-speed, and even endodontic rotary capabilities. These handpieces incorporate motors to operate moving portions, which are regulated by a controller that detects environmental factors and correspondingly powers the motor. Surgical handpiece motors typically function in inherently noisy electronic environments, making the collection an interpretation of environmental and operational data difficult. What is needed in the art, therefore, is a handpiece controller with the capability to collect environmental and operational data from the motor, filter the data, and adjust the operation of the motor based on the filtered environmental data.

SUMMARY OF THE INVENTION

In one embodiment, the present invention relates to a digital controller for a surgical handpiece. The controller is programmable and configurable by software which may be used with a variety of types of handpieces. The controller is equipped with environmental sensors that detect pressure, humidity and temperature. These sensors provide data used for testing and evaluating the function of the handpiece. A filter program is provided which removes electronic noise from collected data.

In an additional embodiment, the controller includes an electronic memory writer and reader to download firmware and control parameters for handpiece operation. Additionally, the reader may read logged data from sensors to determine motor function.

In another embodiment, the controller includes a hermetic enclosure constructed from a heat conducting material. The heat producing components are in direct contact with this material so that heat is directed away from the controller components. The enclosure material is non-ferromagnetic to allow communication between the trigger and controller, and between motor position and controller.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

FIG. 12 is a cross sectional view of a traditional hybrid circuit.

FIG. 13 is a cross sectional view of a heat transfer circuit in accordance with an embodiment of the invention.

DETAILED DESCRIPTION

The present invention is generally directed to a dual processor digital controller that is software programmable and hardware configurable to operate various types of electric powered medical handpieces. The controller includes sensors that detect motor data and environmental data, such as motor rotation and position, temperature and humidity. A filter is provided which process the input data and removes noise for smoother operation.

Figure 1:
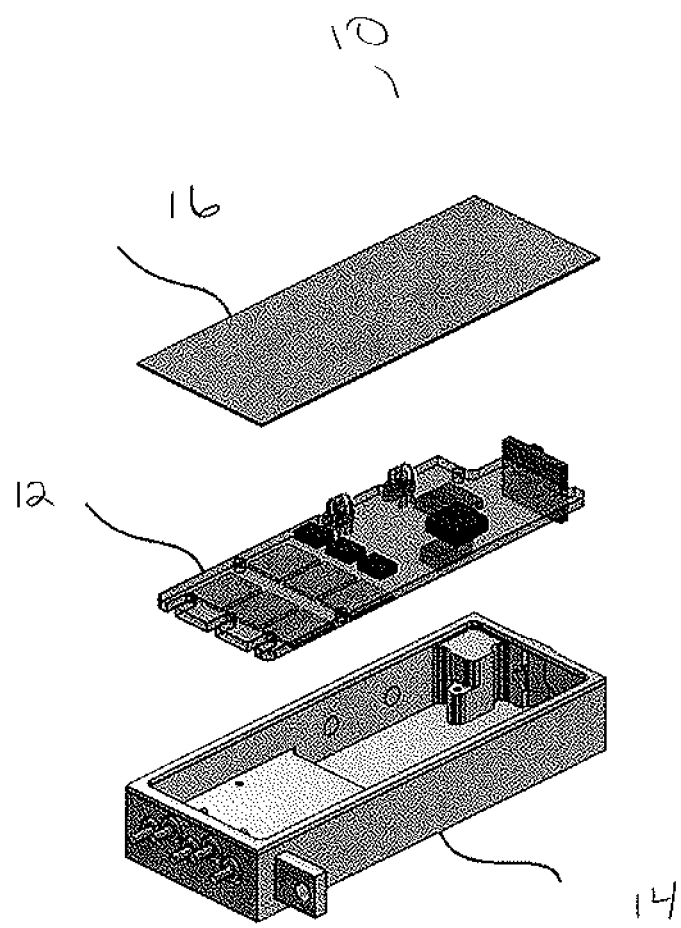
FIG. 1 is a three dimensional perspective view of a controller in accordance with an embodiment of the invention.
Figure 2:
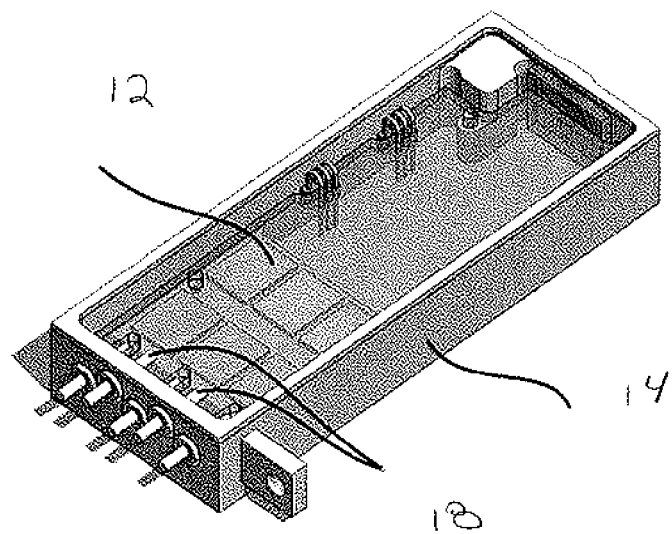
FIG. 2 is a three dimensional perspective view of the internal cavity of a controller in accordance with an embodiment of the invention.
Figure 3:
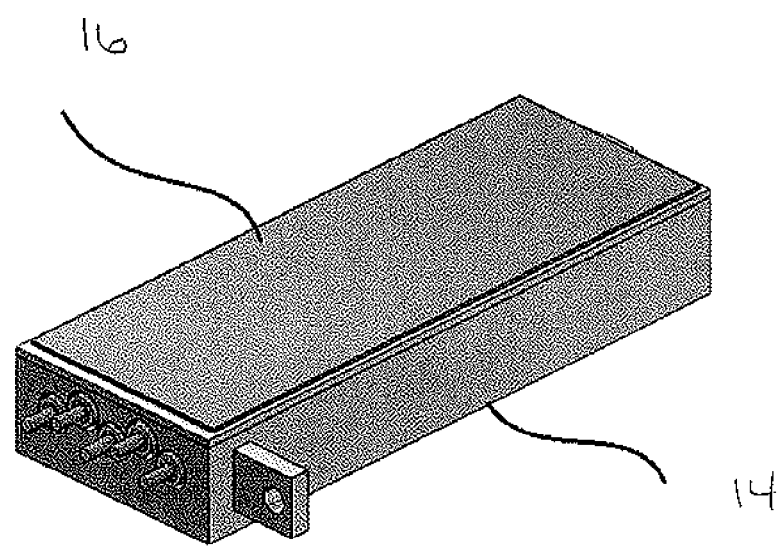
FIG. 3 is a three dimensional perspective view the enclosure of a controller in accordance with an embodiment of the invention.
Figure 4:
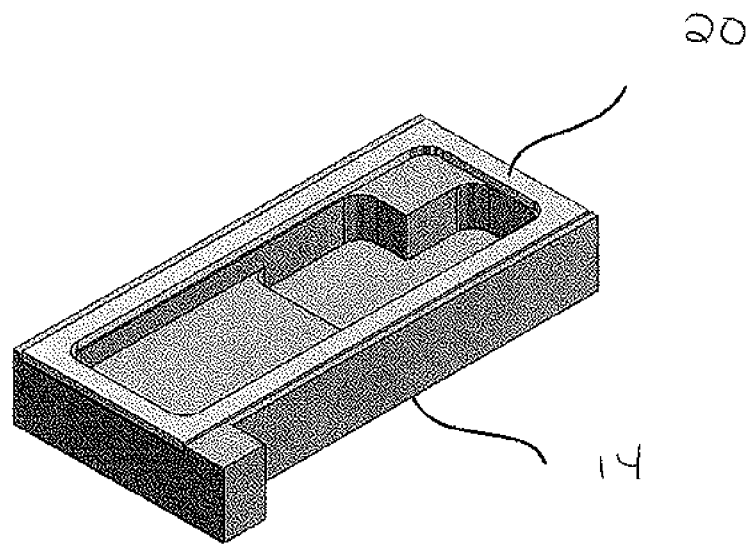
FIG. 4 is an additional three dimensional perspective view of the internal cavity of a controller in accordance with an embodiment of the invention.
Figure 5:
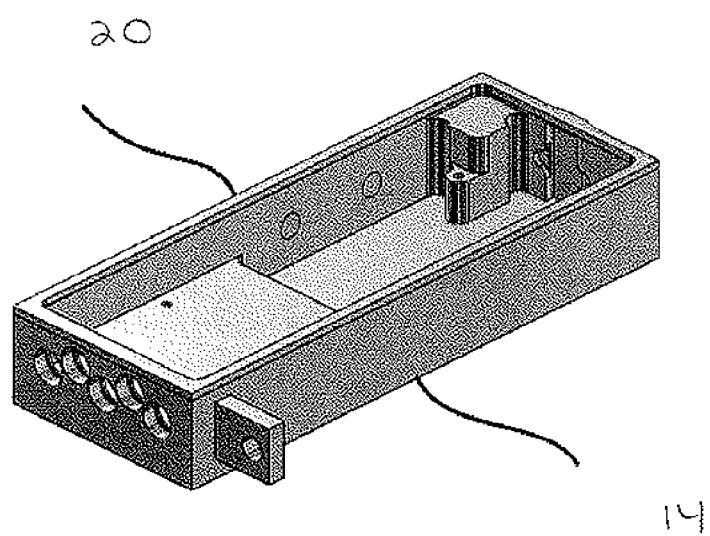
FIG. 5 is an additional three dimensional perspective view of the internal cavity of a controller in accordance with an embodiment of the invention.

FIGS. 1-5 illustrate an embodiment of the controller 10 in the form of a printed control board (PCB) 12 which is housed in a hermetic enclosure 14 with a stainless steel lid 16. The enclosure 14 is constructed from a highly thermally conducting material for dissipating heat produced by the PCB 12. Any components with high heat production are placed in contact with the enclosure 14 for efficient heat dissipation, protecting electrical components from overheating and extending motor run time. The enclosure 14 is constructed from a non-ferromagnetic material to allow communication of trigger and trigger sensors (not shown), as well as motor rotation position and motor sensors (not shown), all magnetic based. In one embodiment, the enclosure 14 is constructed from copper. One of skill in the art will recognize that other materials may be used in the construction of enclosure 14. In an additional embodiment, the enclosure 14 is made from aluminum. Turning now to FIGS. 4 and 5, the enclosure includes a stainless steel rim 20 that is permanently and hermetically fixed to the enclosure 14 by brazing, welding, or other procedures known in the art. The enclosure 14 and lid 16 may be attached by welding or other known technique. In an additional embodiment, the enclosure 14 outer surfaces may be covered in a non-ferromagnetic protective coating to prevent corrosion.

Figure 6:
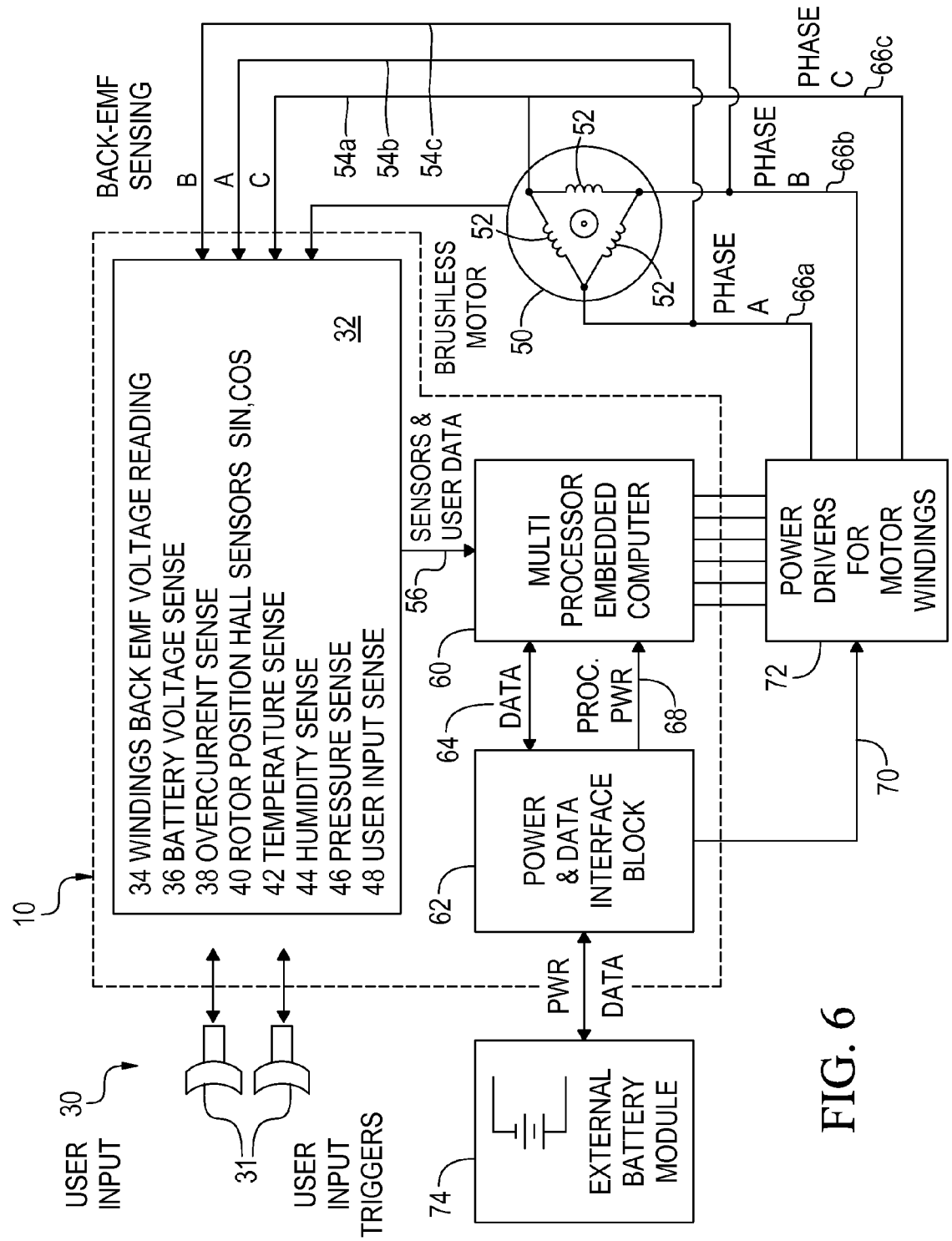
FIG. 6 is a diagram illustrating the controller and other external components in accordance with an embodiment of the invention.

FIG. 6 depicts the controller 10 and several other external components. Collected data is inputted to the controller 10 through user input devices 30. In one embodiment, controller 10 includes an electronic memory writer and reader 32 to download firmware and control parameters to the PCB for handpiece operation and read environmental and operational data from sensors. In an additional embodiment, this data is collected using a handpiece trigger 31 or other apparatus for operating the handpiece. The trigger 31 may, in one example, initiate a cutting instrument on the handpiece, or increase the power to the handpiece. Data collected from the handpiece can include the speed of any cutting implement, the resistance experienced by the device, etc. Other collected data may be collected from motor 50, for instance windings back EMF voltage 34, battery voltage 36, overcurrent information 38 and rotor position 40. In additional, the rotor may also contain sensors that collect environmental data such as temperature 42, humidity 44, pressure 46 or other data 48, as will be discussed in greater detail below.

Turning again to FIG. 6, controller 10 regulates motor 50. In one embodiment, motor 50 is a brushless DC electric motor. Brushless DC electric motors are synchronous motors which are powered by a DC electric source via an integrated inverter/switching power supply, which produces an AC electric signal to drive the motor. Additional sensors and electronics control the inverter output amplitude and waveform frequency (i.e. rotor speed). A brushless motor incorporates permanent magnets (not shown) which rotate and a fixed armature or rotor (not shown).

In an additional embodiment, the brushless motor 50 operates as a stepper motor, dividing rotation into a number of equal steps. Stepper motors have multiple "toothed" electromagnets (not shown) arranged around a central gear-shaped piece of iron (not shown). The electromagnets are energized by an external controller 10. First, one electromagnet is given power, attracting the gear's teeth to the electromagnet's teeth. When the gear's teeth are aligned to the first electromagnet, they are slightly offset from the next electromagnet. The first electromagnet is turned off and the second electromagnet is turned on. The gear rotates slightly to align with the next one, and from there the process is repeated. Each of those slight rotations is called a "step", with an integer number of steps making a full rotation. In this way, the motor can be turned by a precise angle. An electronic controller (i.e., controller 10) continually switches the phase to the windings 52 based on collected data and causes the motor to turn. Brushless motors are efficient and offer reduced electronic noise. In addition, because the windings are supported by the controller housing 14, they are cooled by conduction as will be explained in more detail below. As a result, not airflow is required for cooling.

Permanent-magnet motors, the most common DC motors, generate a voltage when they rotate. This voltage, or "back-EMF" voltage 34, is directly proportional to the motor velocity. Back-EMF 34 is a voltage that occurs in electric motors where there is relative motion between the armature of the motor and the external magnetic field. One practical application is to use this phenomenon to indirectly measure motor speed and position. A motor controller 10 that can accurately sense the back-EMF voltage 34 can determine the motor's velocity. If the back-EMF voltage 34 is integrated over time, the motor's position can be determined as well. In one embodiment of the invention, the motor 50 includes voltage sensors (not shown) which record the back-EMF voltage 34. This data is logged and may be used in the operation of controller 10. One of skill in the art will understand that these voltage sensors may be placed at alternate locations, for instance within the controller 10.

Brushless DC motors are generally three phase devices. They are wired in either a Wye or Delta configuration, but in either case there are three connecting wires 50 (FIG. 6), and the current input to any two coils must be output through the third. The three coils generate the magnetic field of the stator (not shown) (the non-rotating outer portion of the motor), while the rotor magnetic field is created by permanent magnets. The rotor and stator fields interact to create rotational torque, however the timing and relative magnitude of the current through each stator winding must be synchronized with the rotor position to keep the stator electrical field aligned as the rotor rotates. In a brushless DC motor, this synchronization is done by the external controller 10.

In one embodiment, the present invention utilizes three optical position sensors (not shown) to control the motor 50. In this embodiment, Hall sensors are used. It is to be understood that other methods, such as sinusoidal commutation and field oriented control, may also be used to control motor 50 operation. A Hall sensor is a transducer that varies its output voltage in response to a magnetic field and may be used to determine positions, speed and current. As they are most commonly used, these binary sensors define six useable rotation states and a simple table converts the input Hall state to the output motor drive signal for each winding. The information 40 collected from the Hall sensor may be used to determine the position of the permanent magnet and to regulate the speed of the rotor. This data is logged and may be used in the operation of controller 10.

Figure 8:
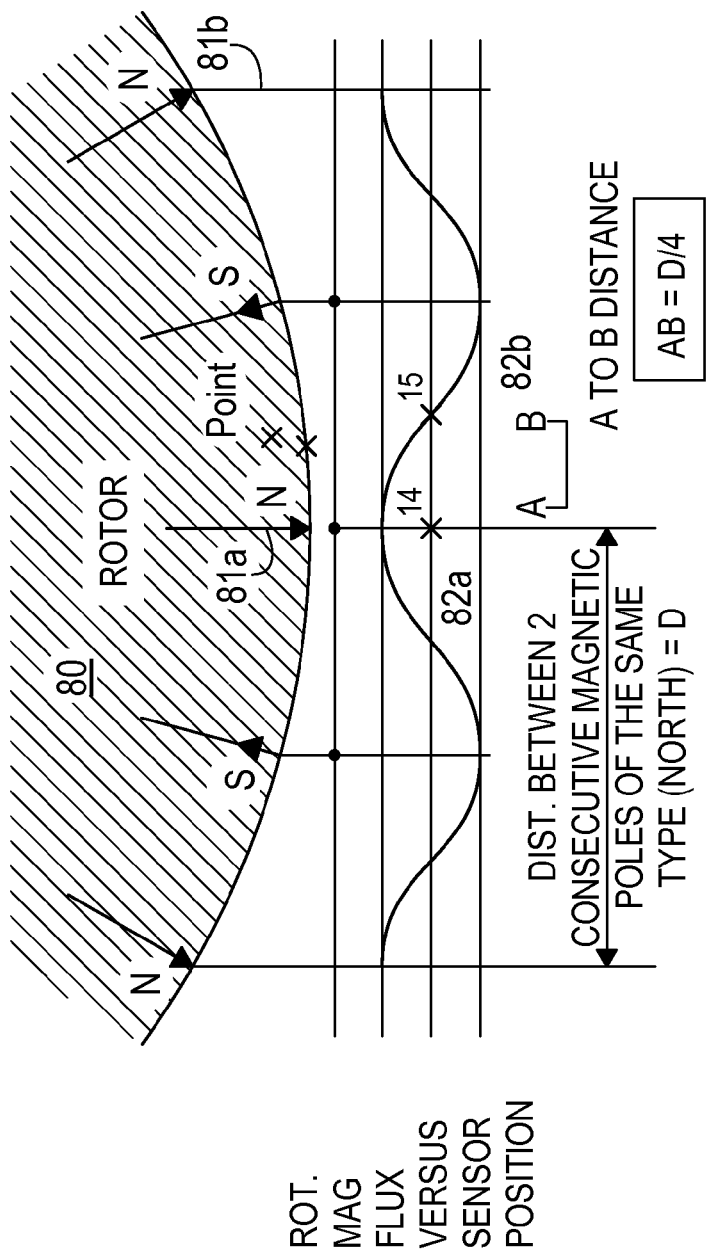
FIG. 8 is a diagram illustrating the placement of Hall sensors on a rotor in accordance with an embodiment of the invention.
Figure 9:
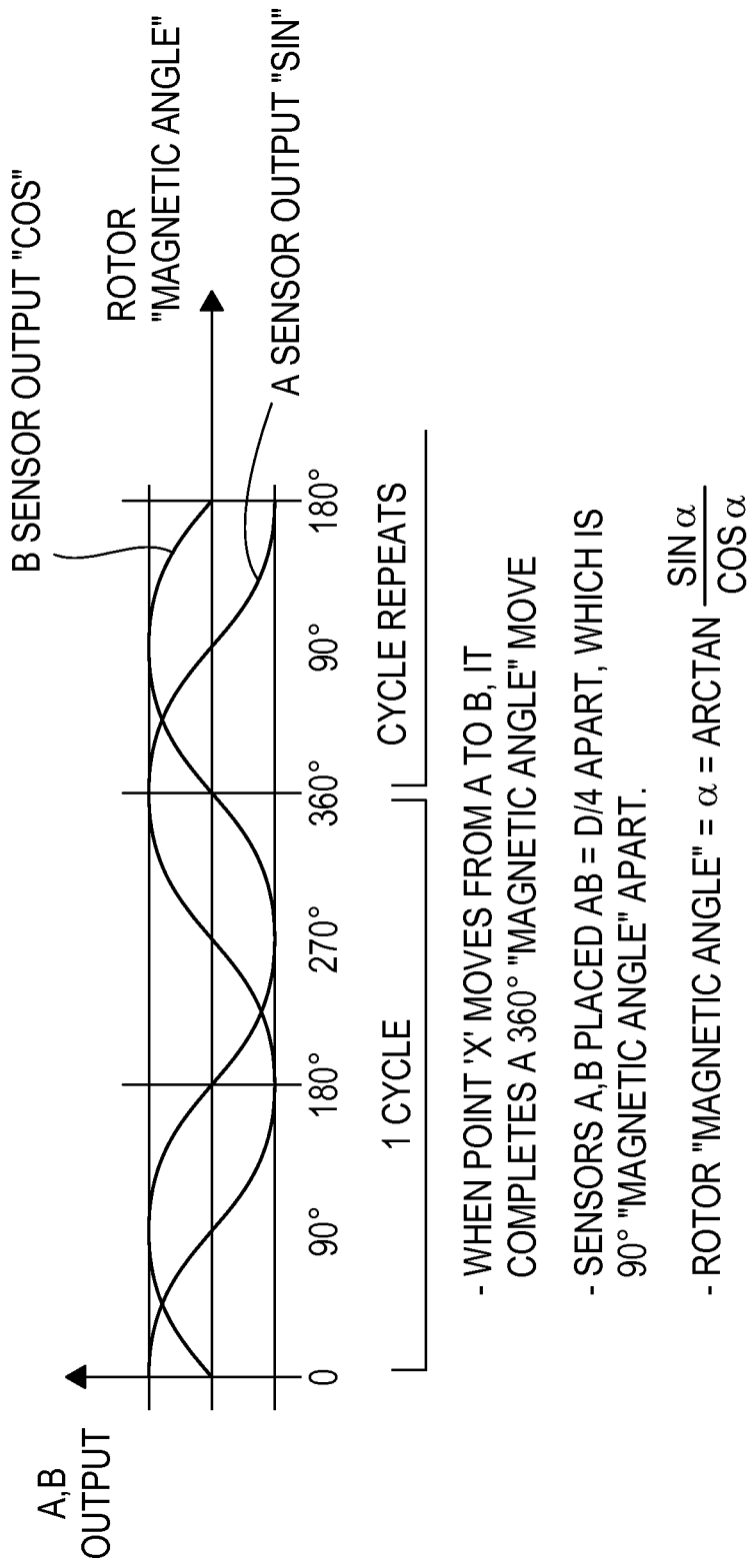
FIG. 9 is a diagram illustration the steps in calculating the rotor angle in accordance with an embodiment of the invention.
Figure 10:
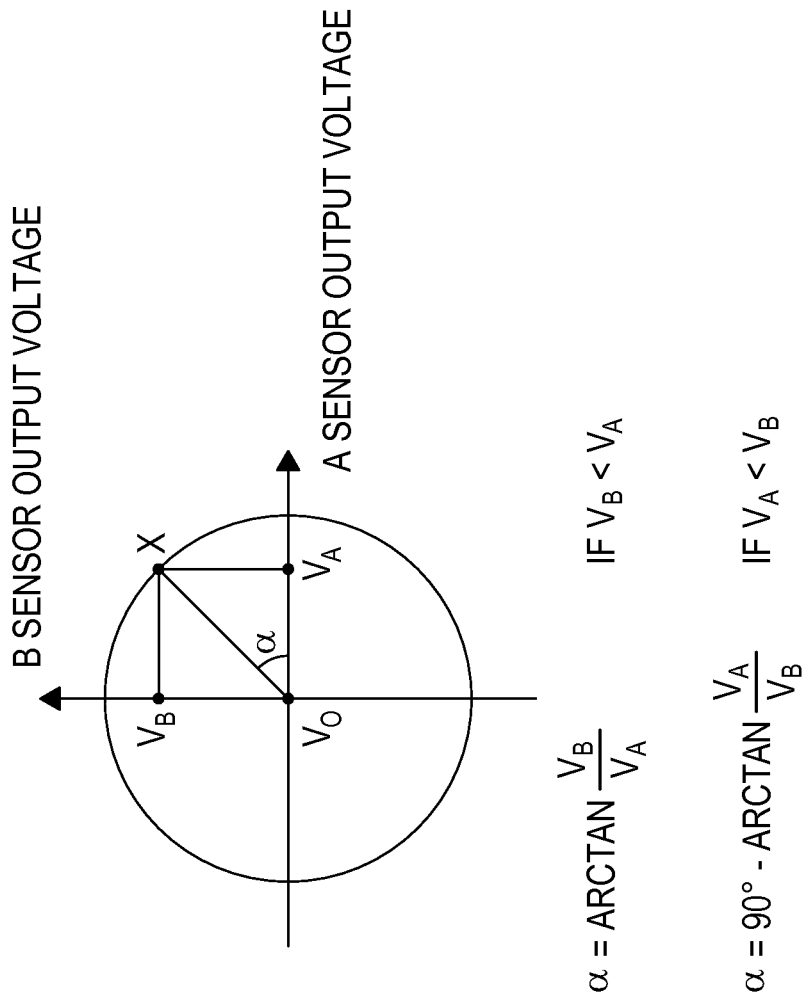
FIG. 10 is an additional diagram illustration the steps in calculating the rotor angle in accordance with an embodiment of the invention.

FIGS. 8, 9 and 10 illustrate how the rotor position is calculated utilizing data collected by the Hall sensors. Briefly, the rotor magnetic angle α is calculated by placing two Hall sensors A (82a) and B (82b) on the rotor. Referring to FIG. 8, the sensors 82a and 82b are placed at a distance AB that is equivalent to ¼ the distance between two consecutive magnetic poles 81a and 81b. The A sensor 82a output is characterized as sin α while the B sensor 82b output is characterized as cos α. Referring now to FIG. 9, when a point X moves from sensor A 82a to sensor B 82b, the rotor magnetic angle α may be calculated as:

$$\alpha = \arctan(\sin\alpha/\cos\alpha) \quad (1)$$

Turning now to FIG. 10, the sensor output voltage may also be used to find the magnetic angle. Specifically:

$$\alpha = \arctan(V_B/V_A) \text{ if } V_B < V_A \quad (2)$$

$$\alpha = 90° - \arctan(V_B/V_A) \text{ if } V_A < V_B \quad (3)$$

This data is logged and may be used in the operation of controller 10.

Figure 11A:
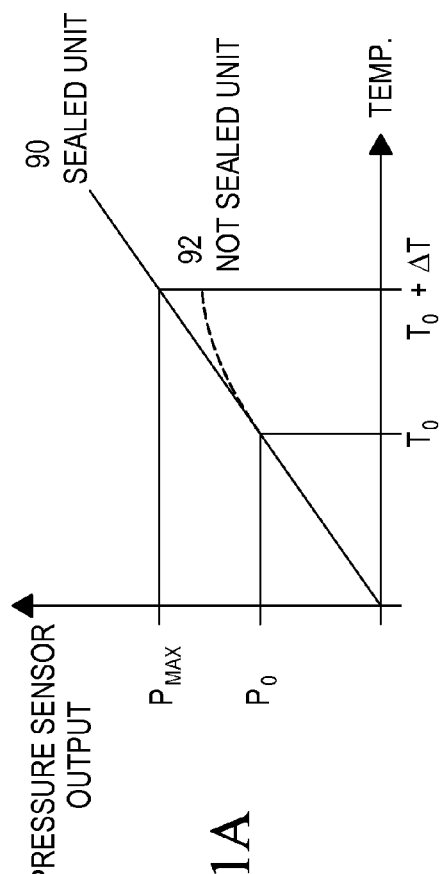
FIG. 11A is a graph of pressure sensor output versus temperature for a sealed and an unsealed controller in accordance with an embodiment of the invention.
Figure 11B:
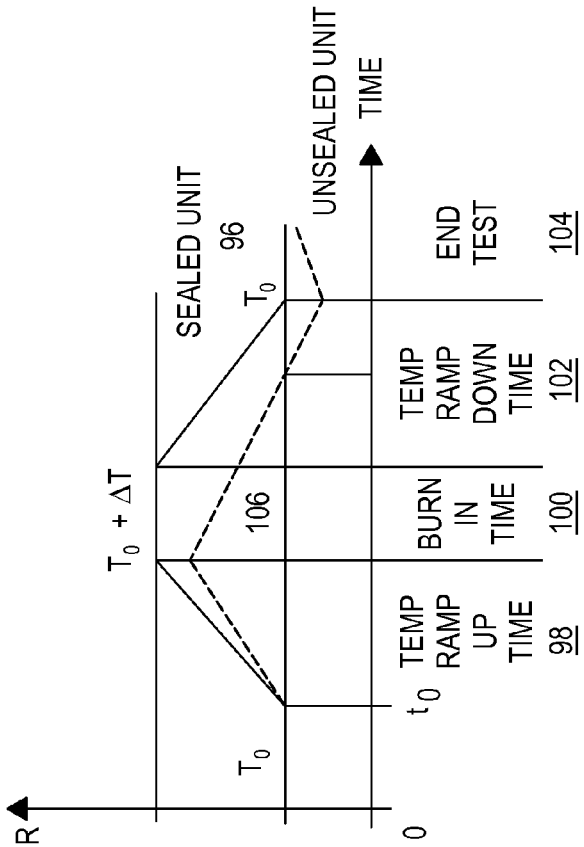
FIG. 11B is an additional graph of pressure sensor output versus temperature for a sealed and an unsealed controller in accordance with an embodiment of the invention.

As illustrated in FIGS. 11A and 11B, environmental information relating to temperature may also be transmitted to the embedded computer 60 (FIG. 6). In one embodiment, temperature 42 and pressure 46 sensors (not shown) are placed within the enclosure 14 (FIG. 6). As discussed above, enclosure is hermetically sealed and includes a stainless steel lid 16 (FIG. 3). FIG. 11A is a plot of pressure 46 v. time as measured by a pressure sensor located within enclosure 14. In a sealed (closed) system, the plot of pressure v. time rises in a linear fashion, as illustrated by line 90. A unit that is not sealed will produce a plot with a non-linear or curved line 92. Similarly, FIG. 11B illustrates a plot of pressure 46 v. time as measured by a pressure sensor located within enclosure 14. Line 96 illustrates a sealed system. Here, the plot increases in a linear fashion during temperature ramp up 98, remains steady during the burn-in time 100, and decreases in a linear fashion during ramp-down time 102. However, in a compromised (non-sealed) controller, the plot decreases during the burn-in time 100, as indicated by line 106. An observed rise in temperature in the hermetic enclosure 14 without a corresponding pressure increase indicates failure of the hermetic seal. FIGS. 11A and 11b indicate that the pressure sensors may transmit pressure data 46 indicative of the integrity of the sealed controller 14. This data is logged and may be used in the operation of controller 10.

In an additional embodiment, the controller 14 further includes one or more humidity sensors (not shown). These sensors will measure the moisture content within the hermetic enclosure 14. A rise in humidity levels indicates fluid intrusion. This data is logged and may be used in the operation of controller 10.

The information regarding operation of the motor 50 (i.e., back-EMF voltage 34 and rotor position 40, as well as battery voltage, 36, overcurrent information 38, temperature 42, humidity 44 and pressure 46 readings) is collected via lines 54a, 54b and 54c and communicated to a multi-processor embedded computer 60 via line 56. Here, the data is filtered to eliminate electronic noise. The noise may be removed using a "filter". In one embodiment, the Kalman filter is utilized to clean up the data. The Kalman filter is an algorithm that uses a series of measurements observed over time, containing noise (random variations) and other inaccuracies, and produces estimates of unknown variables that tend to be more precise than those based on a single measurement alone. Specifically, the Kalman filter operates recursively on streams of noisy input data to produce a statistically optimal estimate of the underlying system state.

After filtering, the data is further transmitted to the power and data interface 62 via line 64, where the data is analyzed. If any changes are required to the speed or power to insure its proper function, the power and data interface block 62 communicates to the winding power drivers 72 any necessary changes to, for instance, the speed or placement of the rotor, as illustrated by line 70. The power drivers 72 increase or decrease the power to the motor (lines 66a, 66b and 66c) in order to keep the motor 50 in phase.

Figure 7:
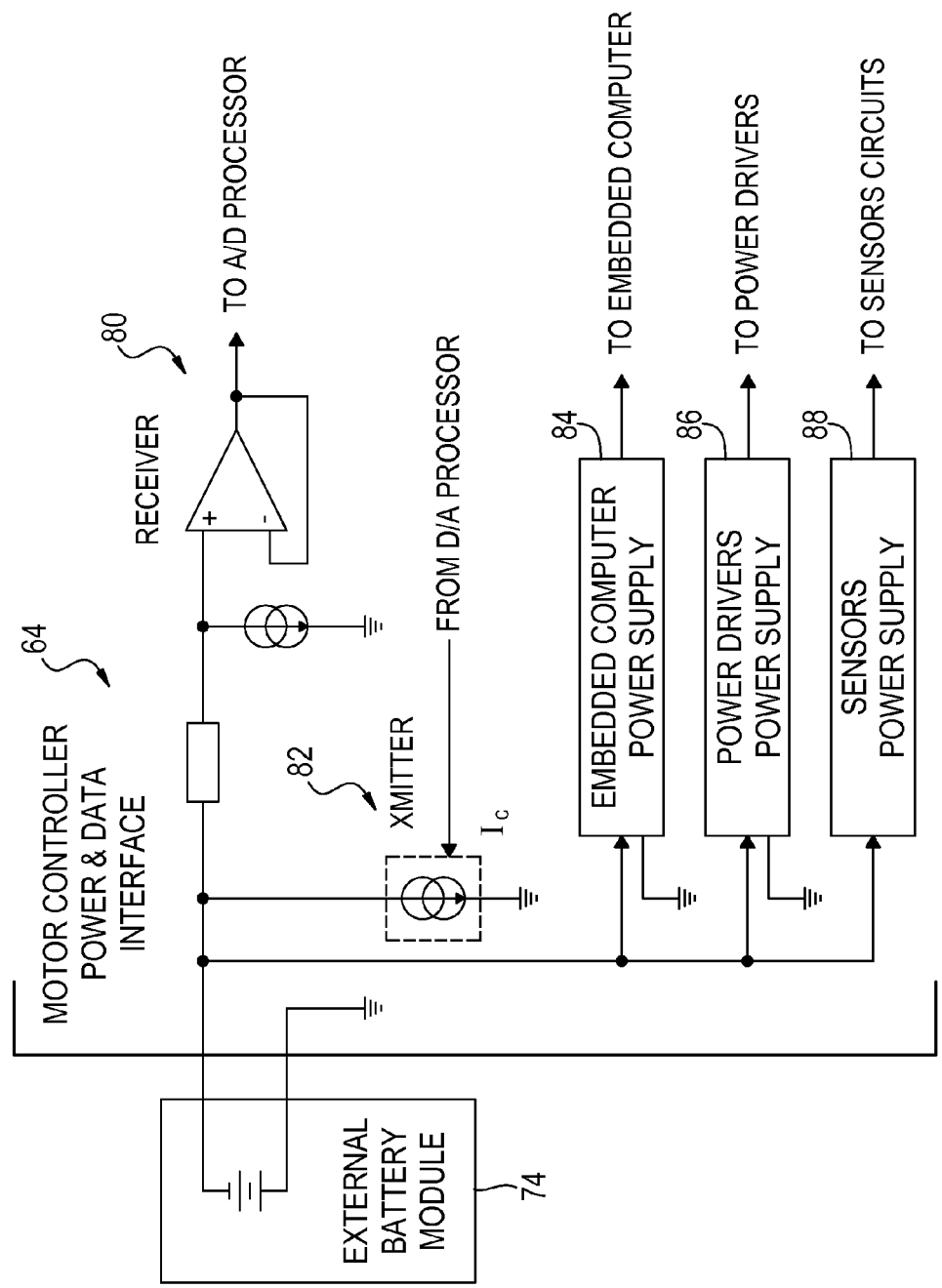
FIG. 7 is a diagram illustrating a power supply in accordance with an embodiment of the invention.

The controller includes an external battery module 74. As illustrated in FIG. 7, battery module 74 supplies power to the controller power and data interface 64, as well as a receiver 80, a transmitter 82. The battery module also acts as an embedded computer power supply 84, a power driver power supply 86 and a sensor power supply 88.

As mentioned previously in reference to FIGS. 1-5, the enclosure 14 is constructed from a highly thermally conducting material for conducting heat produced by controller 10. FIG. 12 illustrates a traditional hybrid circuit that could be utilized in the construction of a PCB controller. Here, the power MOSFETS 112, which have high heat production, are placed upon a circuit trace 114. The circuit trace 114 is a series of copper lines on a printed circuit board 116, often made of a ceramic material. In one embodiment, the circuit trace 114 may be constructed from aluminum. A heat sink is then placed below the ceramic substrate 116. A heat sink is a passive heat exchanger component that cools a device by dissipating heat into the surrounding air. Heat sink materials may include copper and aluminum. In the configuration illustrated in FIG. 12, the excess heat is drawn from the power MOSFETS through the copper traces 114 and ceramic substrate 116, possibly damaging the circuitry of the controller 10. In one embodiment of the invention as shown in FIG. 13, an improved heat transfer circuit includes a heat sink 120 placed above the power MOSFETS 112. The circuit traces 114 sit upon a FR-4 substrate. FR-4 is a composite material composed of woven fiberglass cloth with an epoxy resin binder that is flame resistant. This glass epoxy is a versatile high-pressure thermoset plastic laminate grade with good strength to weight ratios. FR-4 is most commonly used as an electrical insulator possessing considerable mechanical strength and can retain its high mechanical values and electrical insulating qualities in both dry and humid conditions. As a result, the heat from the power MOSFETS is drawn away from the circuit traces and will therefore not damage the controller 10 components.

In one embodiment, controller 10 includes an electronic memory writer and reader 32 to download firmware and control parameters to the PCB for handpiece operation and read environmental and operational data from sensors. In an additional embodiment, the present invention further includes a software programmer in the form of an electronic memory reader/writer which will upload a software program to the controller 10 (FIGS. 1-2) and download logged data from the various environmental sensors 34-38. The programmer communicates with the controller 10 via existing power pins 18 without the requirement of additional data pins.

Figure 14:
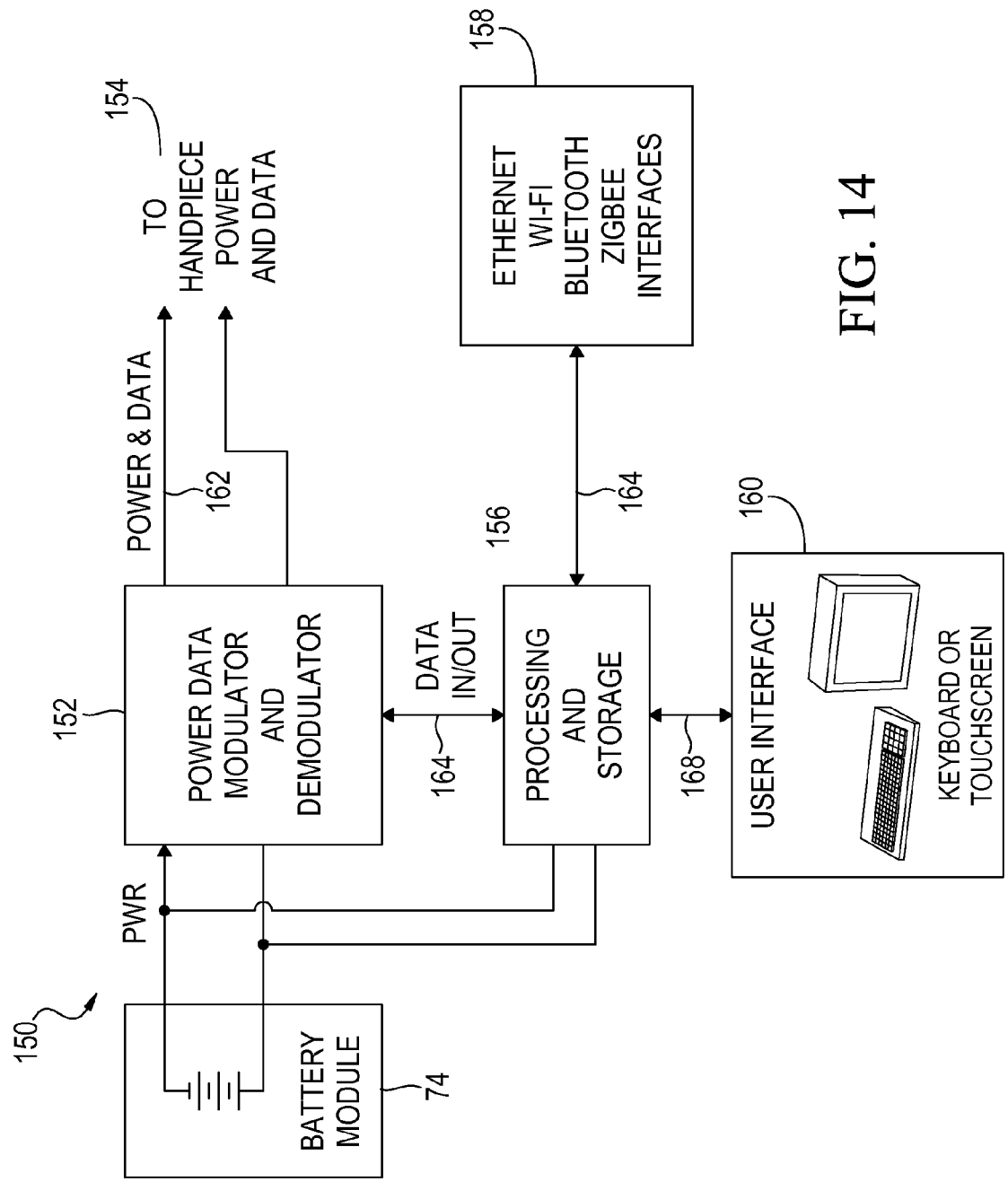
FIG. 14 is a diagram illustrating the Test Program in accordance with an embodiment of the invention.

The invention further provides for a software test program that verifies controller hardware functionality. FIG. 14 illustrates one embodiment of the test program 150. Here, the battery module 74 mentioned previously supplies power to a power data modulator and demodulator 152 and a process and storage device 154. Power and data are transmitted between the modulator/demodulator 152 and the handpiece 154 via line 162. Data is also transferred from the modulator/demodulator 152 to the process and storage device 154 via line 164. The process and storage device 154 then exchanges data with certain external interfaces 158 and a user interface device 160 vial lines 166 and 168, respectively.

Figure 15:
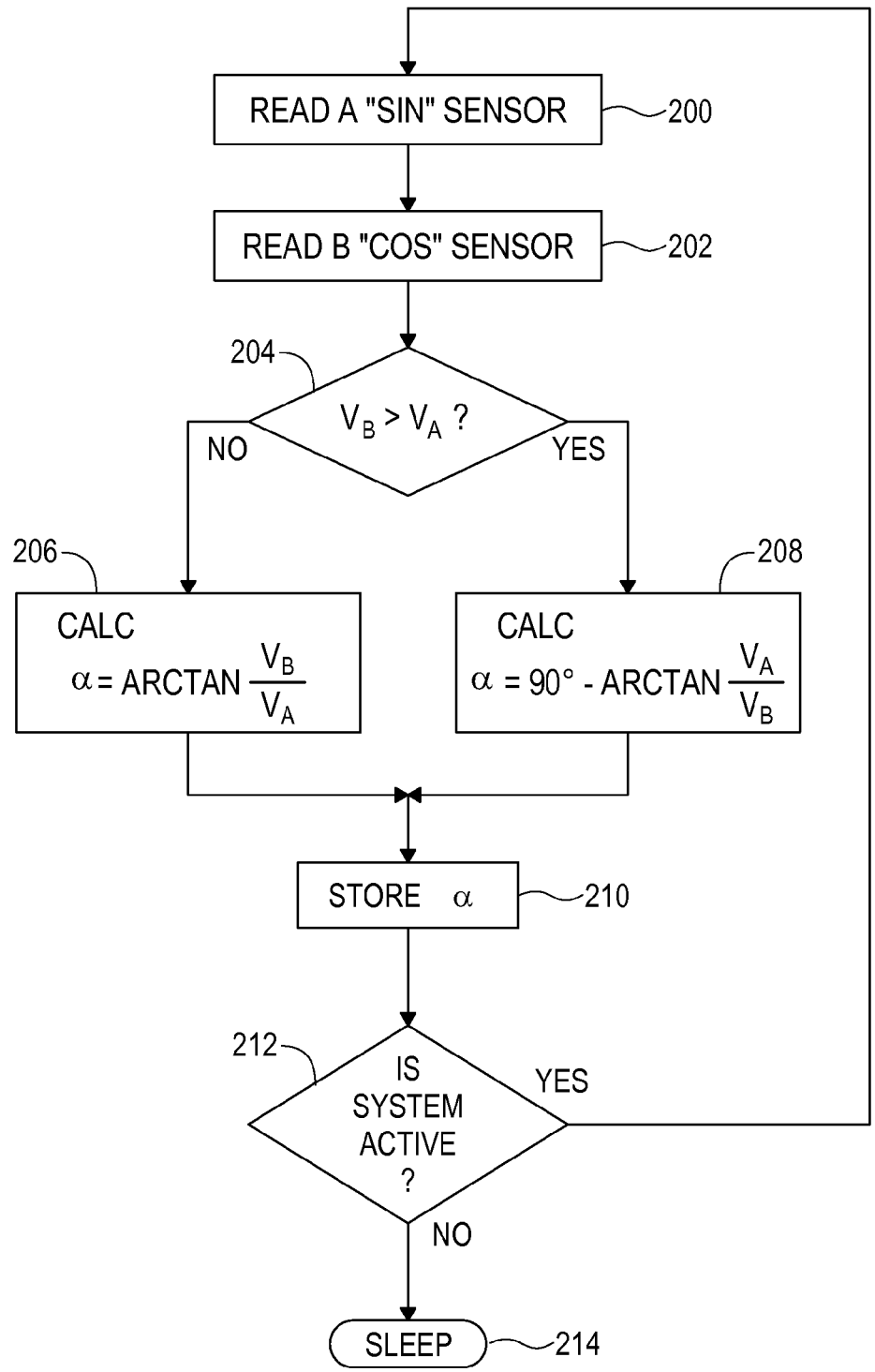
FIG. 15 is a flow diagram showing the steps in determining the rotor angle in accordance with an embodiment of the invention.

FIG. 15 is a flow chart illustrating the method of determining the rotor angle α. As illustrate in blocks 200 and 202, a reading from the A sensor 82a and the B sensor 82b (FIGS. 8 and 9) are collected. The voltage readings $V_A$ and $V_B$ are compared at block 204 and the angle α calculated using either Equation 2 (block 206) or Equation 3 (block 208) as illustrated above. The angle α is stored as illustrate in block 120. If the system is active, i.e., not in test mode and currently powering a motor, the determination of the rotor angle α continues 212. The stored information may be transmitted to the multiprocessor embedded computer 60 (FIG. 1) and analyzed to determine proper rotor function, as explained in more detail below. If the system is not active, it enters a sleep mode 214 to conserve power.

Figure 16:
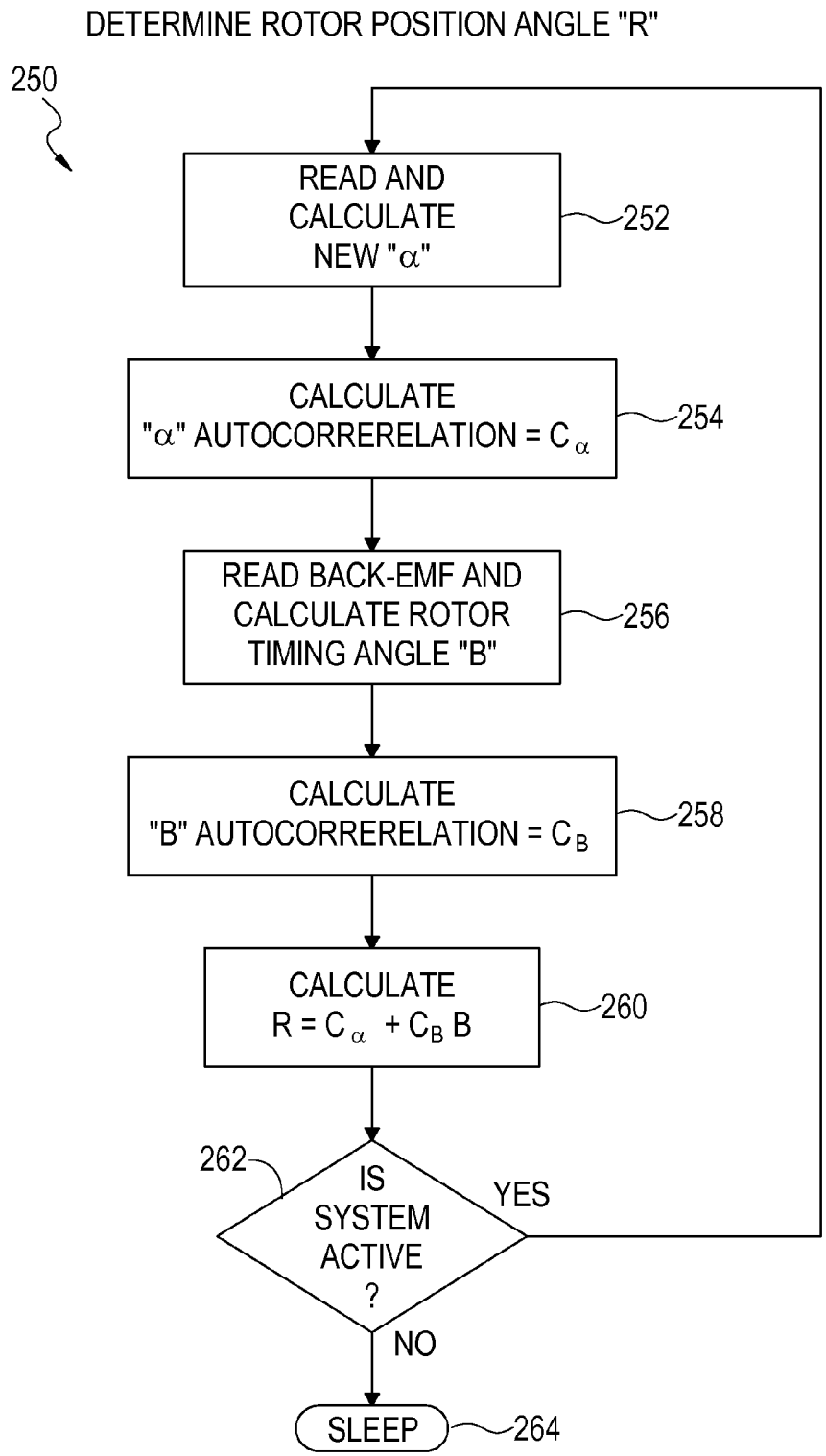
FIG. 16 is a flow diagram showing the steps in determining the rotor position angle in accordance with an embodiment of the invention.

Continuing now to FIG. 16, the rotor position angle R is calculated using the data collected from the Hall sensors and the motor voltage sensors described in detail above. As illustrated by block 252, the rotor angle α is read and calculated as described with reference to FIG. 14. The α autocorrection (Cα) is then calculated based upon the collected data 254. Next, the back-EMF voltage readings are collected from the motor voltage sensors and the rotor timing angle β calculated 256. Block 258 specifies the calculation of the β autocorrection value ($C_\beta$). The rotor position angle R is then calculated a block 260 using the following equation:

$$R = C\alpha \cdot \alpha + C_\beta \cdot \beta \quad (4)$$

If the system is active, i.e., not in test mode and currently powering a motor, the determination of the rotor position β continues 262. The stored information may be transmitted to the multiprocessor embedded computer 60 (FIG. 1) and analyzed to determine proper rotor function, as explained in more detail below.

Figure 17:
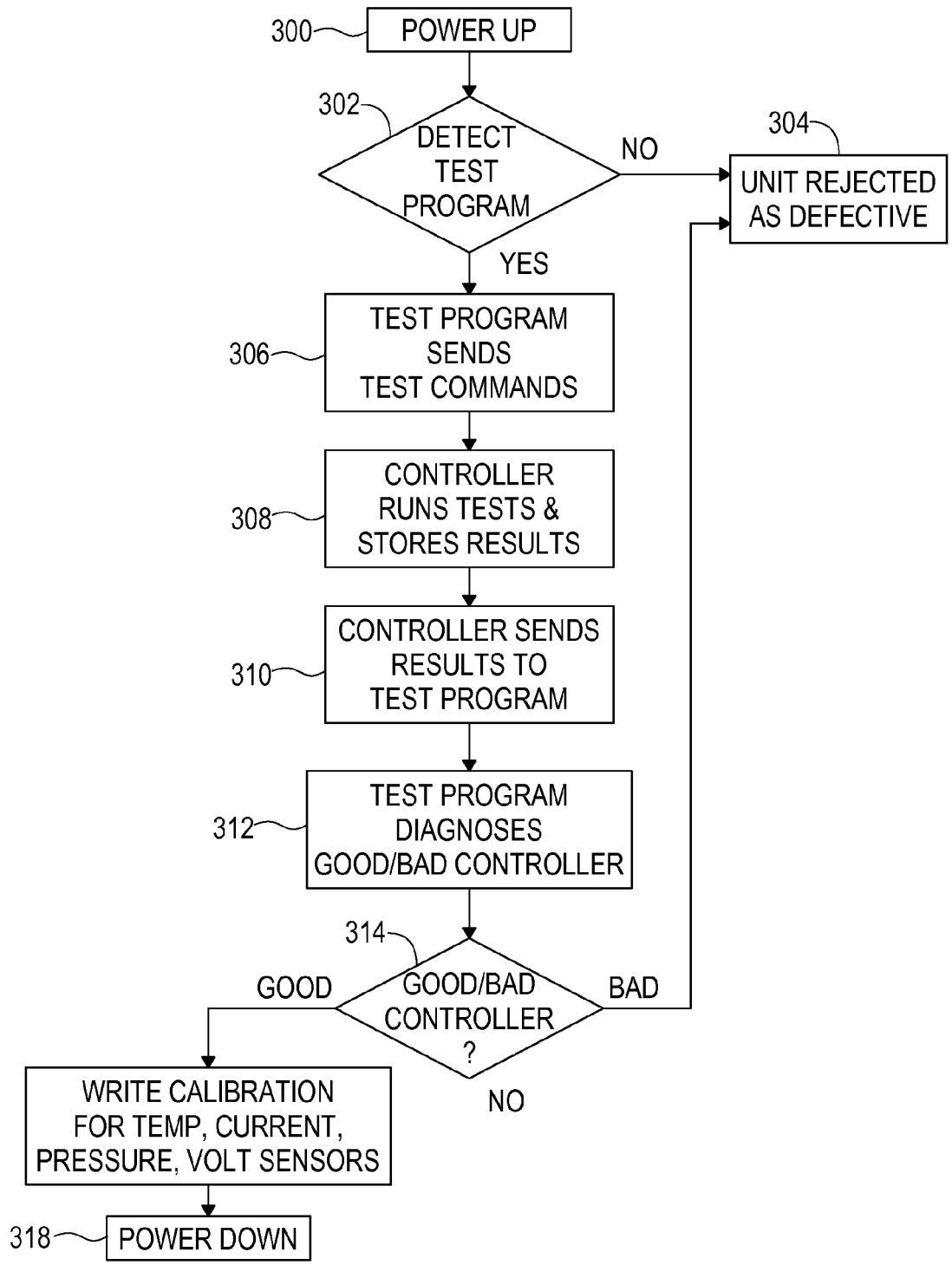
FIG. 17 is a flow diagram showing the steps in the final quality control protocol in accordance with an embodiment of the invention.

In one embodiment, the software Test Program discussed above calibrates trigger travel and, in the case of a two-trigger system, automatically compensates for cross talk. The Test Program simulates outputs to motor lead wires which are scaled and fed back as input signals to trigger and motor sensor inputs to the controller 10, thereby performing a loop-back test of the main signal path. As illustrated by FIG. 17, this software test phase may be performed at the controller manufacturer to confirm hardware functionality. Here, power is supplied to the unit 300, and the unit attempts to detect the Test Program 302. As indicated in block 304, failure to detect the Test Program results in the unit being rejected as defective. If detection occurs, the Test Program sends test commands to the controller 306, and the controller then runs the tests and stores the results 308, and then sends the results back to the Test Program 310. Referring to block 310, the Test Program analyzes the data received from block 310 and determines if the controller is functional. Moving to block 314, any non-functional controller is rejected as defective. If the controller is functioning properly, the calibration data collected from temperature, voltage current and pressure sensors is saved (block 316) at which time the device powers down 318.

Figure 18:
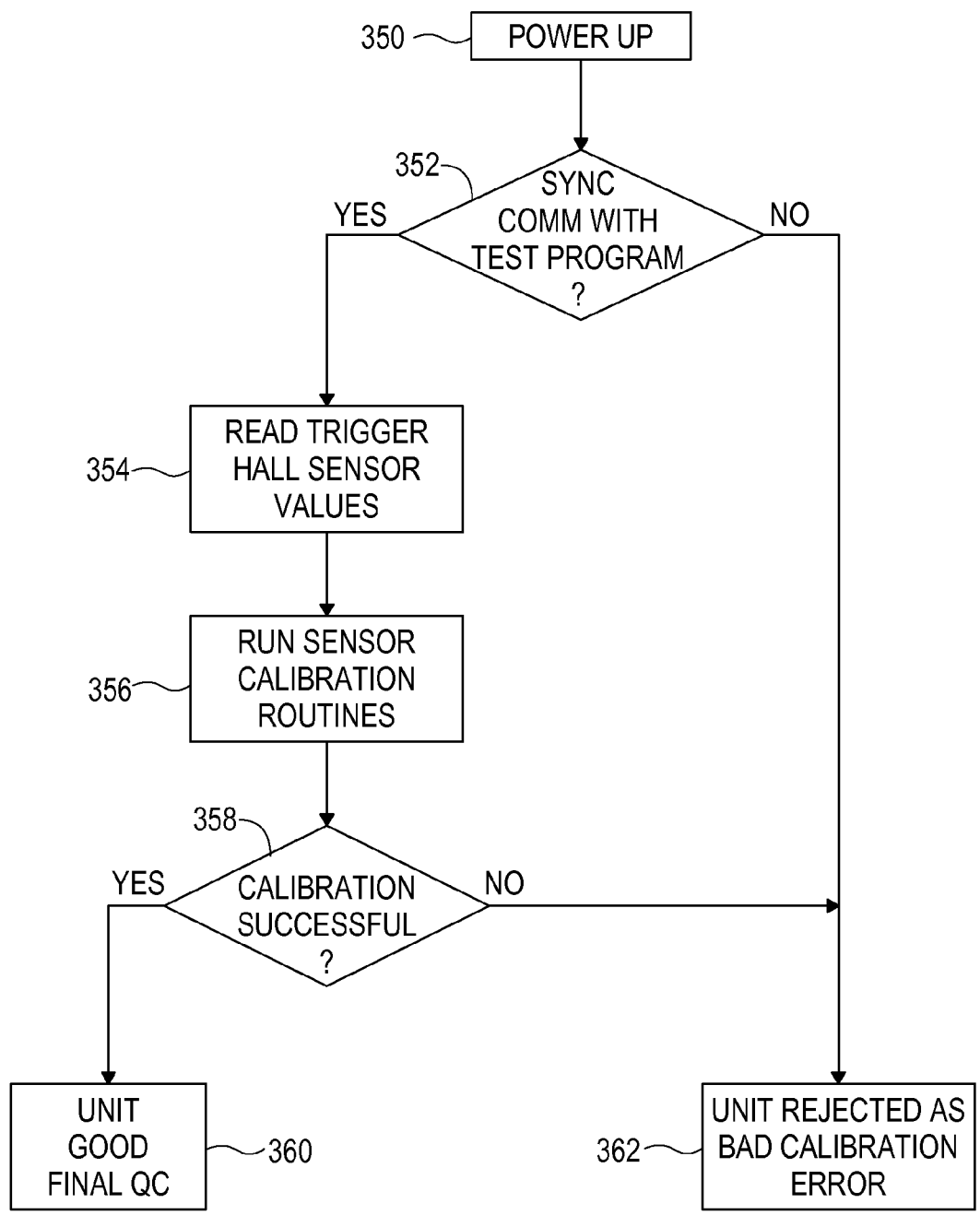
FIG. 18 is an additional flow diagram showing the steps in the final quality control protocol in accordance with an embodiment of the invention.

FIG. 18 illustrates the final for the Test Program protocol. This software test phase may also be performed at the controller manufacturer to confirm hardware functionality. Here, power is supplied to the unit 350 which then attempts to communicate with the self-test software 352. If the unit cannot synchronize with the self-test software, the unit is rejected as defective as indicated in block 362. If synchronization is successful, the trigger and hall sensor data is read 354 and the calibration routines are activated 356. As indicated by block 358, unsuccessful calibration leads to rejection of the unit. Successful calibration indicates that the unit has passed all quality control tests 360. This test verifies operation of the controller and other hardware.

Figure 19:
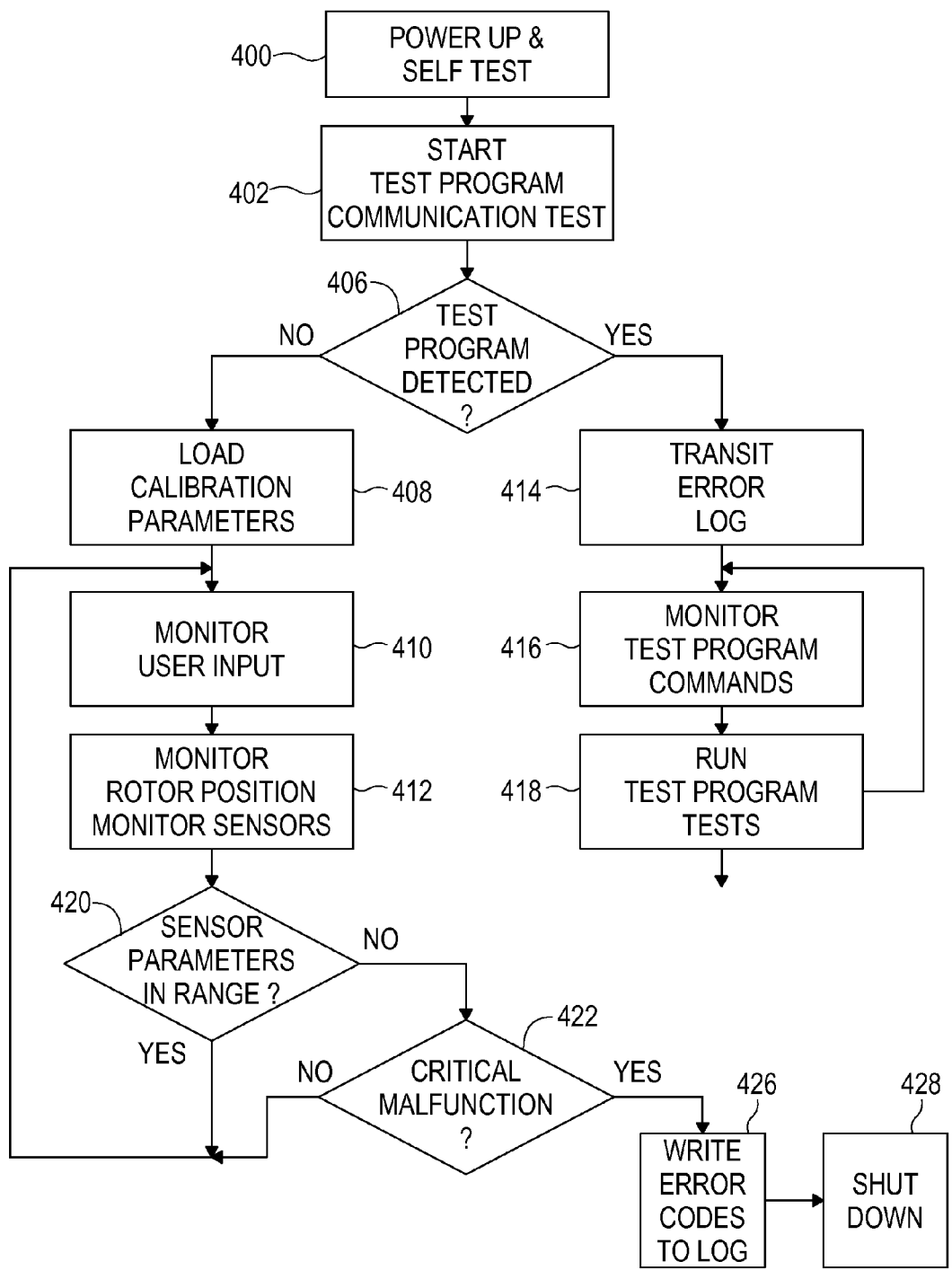
FIG. 19 is an operational flow chart illustrating initiation of the Test Program and controller tests.

This software test may again be performed at the point of use prior to uploading final operating software and installation into a handpiece. FIG. 19 is a flow diagram showing the steps to initiate the Test Program and controller tests. As illustrated in block 402, power is supplied to the unit and a self-testing sequence is initiated. The controller then attempts to communication with the Test Program (blocks 402 and 404). If this attempt is unsuccessful, the unit is ready for use in a medical procedure. Calibration parameters are loaded (block 408), user input 410 and the rotor position 412 sensors are monitored. If the sensor parameters are within range 420, monitoring of user input 410 and the rotor position 412 continues. If the sensor parameters travel outside of an acceptable range, the controller then determines if a critical malfunction has occurred 422. If there is no critical malfunction 422, the controller continues to monitor the sensor parameters. If a critical malfunction has occurred, an error code is written to the log 426 and the unit shuts down. Returning again to block 406, if the Test Program is detected, an error message is logged 414, the Test Program Parameters are monitored 416, and additional Test Program Tests are initiated 418.

The appropriate firmware may be uploaded to controller memory depending on the surgical handpiece type and model, such as drills, sagittal saws and reciprocating saws. Software detects input signals from the trigger and motor sensors and produces corresponding output signals to the motor lead wires which control the direction, speed and power of the electric motor.

The invention claimed is:

1. A digital controller for operating a powered surgical handpiece, comprising
   a printed circuit board;
   a first environmental sensor;
   at least one operational sensor;
   a software program for the operation of the handpiece and for the collection of data, the software program including an electronic filter program; and
   an electronic memory writer and reader,
   wherein the controller is housed within a hermetic enclosure,
   wherein the first environmental sensor is configured for sensing a first environmental condition within the hermetic enclosure and selected from the group consisting of a temperature sensor, a humidity sensor and a pressure sensor.

2. The digital controller of claim 1, wherein the at least one operational sensor is a Hall sensor.

3. The digital controller of claim 1, wherein the hermetic enclosure is constructed from a thermally conducting material.

4. The digital controller of claim 3, wherein the thermally conducting material is selected from the group consisting of copper and aluminum.

5. The digital controller of claim 3, wherein the hermetic enclosure is constructed from a non-ferromagnetic material.

6. The electronic controller of claim 1, wherein the controller switches the phases of a motor.

7. The controller of claim 1, wherein the electronic memory writer and reader uploads software to the controller.

8. The controller of claim 1, wherein the electronic memory writer and reader downloads data from the environmental and operational sensors to the controller.

9. The controller of claim 1, further comprising a software test program to verify the functionality of the controller.

10. The controller of claim 1 wherein the at least one operational sensor is a voltage sensor configured for sensing a back-EMF voltage of a motor of the powered surgical handpiece and the software program is configured for using the back-EMF voltage to calculate a motor velocity and a motor position of the motor.

11. The controller of claim 1 wherein, when the first environmental sensor is a temperature sensor and the first environmental condition is a temperature of an interior of the hermetic enclosure, further comprising a second sensor which is a pressure sensor configured for measuring an air pressure within the hermetic enclosure.

12. The controller of claim 11 wherein the software program is configured for testing the integrity of the hermetic enclosure utilizing data collected by the first sensor and the second sensor.

13. The controller of claim 1 wherein the first sensor is a humidity sensor and the first environmental condition is a humidity level within the hermetic enclosure.

14. A digital controller for operating a powered surgical handpiece, comprising
   a printed circuit board;
   a temperature sensor;
   a pressure sensor;
   a software program for the operation of the handpiece and for the collection of data; and
   an electronic memory writer and reader,
   wherein the controller is housed within a sealed enclosure, and
   wherein the temperature sensor is configured for sensing a first environmental condition within the sealed enclosure and the second sensor is configured for sensing a second environmental condition within the sealed enclosure.

15. The controller of claim 14 comprising a humidity sensor configured for sensing a third environmental condition within the sealed enclosure.

* * * * *